(12) United States Patent
Matievich, Jr. et al.

(10) Patent No.: US 8,301,395 B2
(45) Date of Patent: Oct. 30, 2012

(54) ANALYTE TESTING SYSTEMS

(75) Inventors: William Matievich, Jr., Alameda, CA (US); Alexander G. Ghesquiere, San Francisco, CA (US); Ting Chen, Cedar Park, TX (US)

(73) Assignee: Abbott Diabetes Care Inc., Alameda, CA (US)

(*) Notice: Subject to any disclaimer, the term of this patent is extended or adjusted under 35 U.S.C. 154(b) by 294 days.

(21) Appl. No.: 12/564,372

(22) Filed: Sep. 22, 2009

(65) Prior Publication Data
US 2010/0262380 A1   Oct. 14, 2010

Related U.S. Application Data

(60) Provisional application No. 61/099,184, filed on Sep. 22, 2008.

(51) Int. Cl.
*G06F 19/00*   (2011.01)
(52) U.S. Cl. ............................... 702/22; 702/30; 600/347
(58) Field of Classification Search .................... 702/22, 702/23, 25, 27, 30–32; 435/14; 600/347, 600/365
See application file for complete search history.

(56) References Cited

U.S. PATENT DOCUMENTS

| | | | | |
|---|---|---|---|---|
| 7,138,089 B2* | 11/2006 | Aitken et al. | ............... | 422/82.01 |
| 7,303,726 B2* | 12/2007 | McAllister et al. | ........... | 422/68.1 |
| 8,001,825 B2* | 8/2011 | Pugh et al. | ................. | 73/1.02 |
| 2004/0055898 A1 | 3/2004 | Heller et al. | | |
| 2004/0138588 A1 | 7/2004 | SAikley et al. | | |
| 2005/0164322 A1 | 7/2005 | Heller et al. | | |
| 2005/0239156 A1 | 10/2005 | Drucker et al. | | |
| 2005/0245844 A1 | 11/2005 | Mace et al. | | |
| 2005/0277164 A1 | 12/2005 | Drucker et al. | | |
| 2006/0010098 A1 | 1/2006 | Goodnow et al. | | |
| 2006/0024774 A1 | 2/2006 | Zocchi et al. | | |
| 2006/0030049 A1 | 2/2006 | Bhimani et al. | | |
| 2006/0191787 A1 | 8/2006 | Wang et al. | | |
| 2006/0226985 A1 | 10/2006 | Goodnow et al. | | |
| 2007/0149897 A1 | 6/2007 | Ghesquiere et al. | | |
| 2007/0237678 A1 | 10/2007 | Roesicke et al. | | |
| 2008/0017522 A1 | 1/2008 | Heller et al. | | |
| 2008/0021291 A1 | 1/2008 | Zocchi | | |
| 2008/0021295 A1 | 1/2008 | Wang et al. | | |
| 2008/0021493 A1 | 1/2008 | Levaughn et al. | | |
| 2008/0027302 A1 | 1/2008 | Buse et al. | | |
| 2008/0033318 A1 | 2/2008 | Mace et al. | | |
| 2008/0167578 A1 | 7/2008 | Bryer et al. | | |
| 2008/0188732 A1 | 8/2008 | Mace et al. | | |
| 2009/0018411 A1 | 1/2009 | Mace et al. | | |
| 2009/0099437 A1 | 4/2009 | Yuzhakov et al. | | |
| 2009/0270765 A1 | 10/2009 | Ghesquiere et al. | | |
| 2010/0095229 A1 | 4/2010 | Dixon et al. | | |

OTHER PUBLICATIONS

Extended European Search Report for European Application No. 09252257.2, dated Oct. 12, 2011.

* cited by examiner

*Primary Examiner* — Manuel L Barbee
(74) *Attorney, Agent, or Firm* — Edward J. Baba; Marcus T. Hunt; Bozicevic, Field & Francis LLP

(57) ABSTRACT

The present invention includes analyte measurement systems, analyte measurement meters, analyte testing devices, cartridges thereof and integrated circuits for use therewith, and further includes methods related to the use of the integrated circuits and, in certain embodiments, to the counting or tracking of parameters related to the cartridges and analyte test devices.

52 Claims, 4 Drawing Sheets

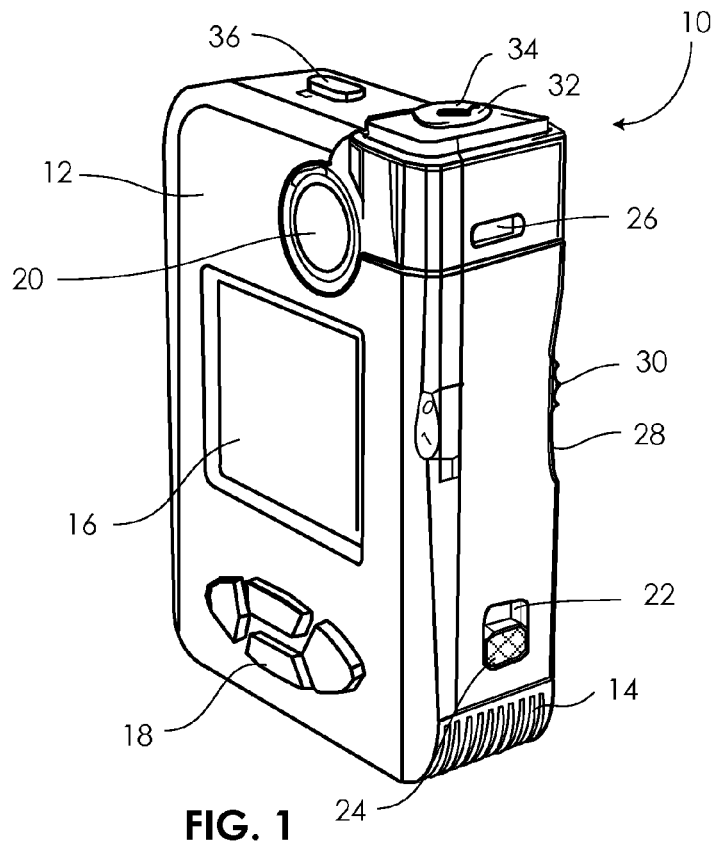
FIG. 1
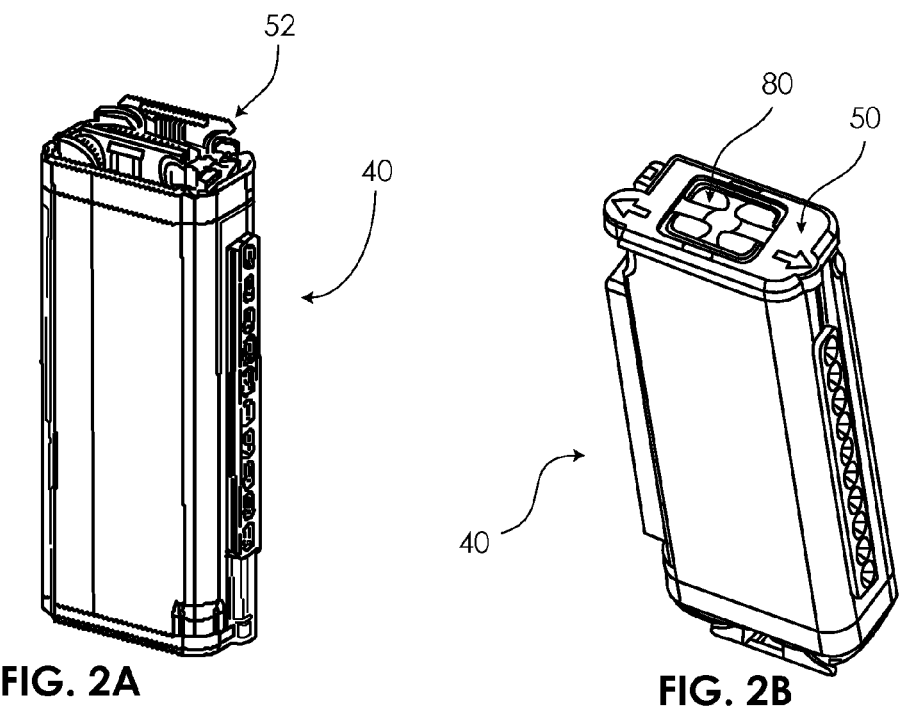
FIG. 2A
FIG. 2B

CARTRIDGE LOG

| Byte Number | Details | Description | Usage |
|---|---|---|---|
| 1 | Usage Days | Indicates the number of days for which the cartridge was present in the device | Actual number of days the cartridge remains in the meter. Updated Daily |
| 2 | Strip Lot Number (MSB) | Cartridge dependent. This may be available in the cartridge installed. This may be updated at the factory level. | To know the measurement parameters loaded in the Smart Chip. The measurement parameters may be read from the data base using the strip lot number. |
| 3 | Strip Lot Number | | |
| 4 | Strip Lot Number | | |
| 5 | Strip Lot Number | | |
| 6 | Strip Lot Number (LSB) | | |
| 7 | Installation Date (MSB) | Represent the date of installation. | To identify the frequency of the cartridge usage. |
| 8 | Installation Date (LSB) | | |
| 9 | Strips Remaining | Indicates the number of strips left in the cartridge at the time of removal of the cartridge. | Used to know the number of strips that is being used effectively. |
| 10 | Status Information | This byte may be used to indicate the type of expiry and if the cartridge was installed New or Used. | To know the reason for the cartridge expiry and whether the cartridge installed is unused or used |
| 11 | 16 Bit ID – (MSB) | Unique ID in Cartridge | To Track Cartridges in the meter |
| 12 | 16 Bit ID – (LSB) | | |
| 13 | 16 Bit ID – (MSB) | Time Cartridge Removed | To be able to add to tub open time if cartridge is returned to the meter |
| 14 | 16 Bit ID - | | |
| 15 | 16 Bit ID - | | |
| 16 | 16 Bit ID – (LSB) | | |
| 17 | 16 Bit CRC – (MSB) | CRC to check the data integrity of the log. | To maintain the data integrity of the cartridge log. |
| 18 | 16 Bit CRC – (LSB) | | |

FIG. 5

ANALYTE TESTING SYSTEMS

CROSS REFERENCE TO RELATED APPLICATIONS

This application claims the benefit of U.S. Provisional Patent Application Ser. No. 61/099,184, filed on Sep. 22, 2008, and is related to U.S. patent application Ser. Nos. 10/837,886 published as US2005/0245844; 10/899,773 published as US2006/0024774; 11/830,760; 11/830,779; 11/830,786; 11/831,706; 11/535,985; 11/535,986 published as US2007/0079783; 11/035,131 published as 2005/0164322, 11/831,649 published as 2008/0033318, 11/868,762, 11/350,398, 12/035,348, 11/830,770, 10/701,993 published as 2004/0138588, 12/185,116; 12/185,117; 12/233,584 and 12/185,118; as well as PCT applications PCT/US2005/014855; WO2006/19665; WO2008/39946; and WO2008/39949; and EP1779109; which are each assigned to the same assignee as the present application and are hereby incorporated by reference.

FIELD OF THE INVENTION

The invention relates to analyte testing systems, and particularly to managing information relating to analyte test strips and/or containers thereof. Such information may include expiration criteria for the strips for maintaining along with unique identifiers for the strips and/or containers of strips.

BACKGROUND OF THE INVENTION

There are a number of instances when it is desirable or necessary to test or monitor the concentration of an analyte, such as glucose, lactate, or oxygen, for example, in bodily fluid of a body. Bodily sample analyte tests are routinely conducted in a variety of medical settings (e.g., doctor's office, clinic, hospital, by medical personnel) and in the home by the patient and/or a caretaker. For example, it may be desirable to monitor high or low levels of glucose in blood or other bodily fluid that may be detrimental to a human. In a healthy human, the concentration of glucose in the blood is maintained between about 0.8 and about 1.2 mg/mL by a variety of hormones, such as insulin and glucagons, for example. If the blood glucose level is raised above its normal level, hyperglycemia develops and attendant symptoms may result. If the blood glucose concentration falls below its normal level, hypoglycemia develops and attendant symptoms, such as neurological and other symptoms, may result. Both hyperglycemia and hypoglycemia may result in death if untreated. Maintaining blood glucose at an appropriate concentration is thus a desirable or necessary part of treating a person who is physiologically unable to do so unaided, such as a person who is afflicted with diabetes mellitus.

The most important factor for reducing diabetes-associated complications is the maintenance of an appropriate level of glucose in the blood stream. The maintenance of the appropriate level of glucose in the blood stream may prevent and even reverse some of the effects of diabetes. Certain compounds may be administered to increase or decrease the concentration of blood glucose in a body. By way of example, insulin can be administered to a person in a variety of ways, such as through injection, for example, to decrease that person's blood glucose concentration. Further by way of example, glucose may be administered to a person in a variety of ways, such as directly, through injection or administration of an intravenous solution, for example, or indirectly, through ingestion of certain foods or drinks, for example, to increase that person's blood glucose level.

Regardless of the type of adjustment used, it is typically desirable or necessary to determine a person's blood glucose concentration before making an appropriate adjustment. Typically, blood glucose concentration is monitored by a person or sometimes by a physician using an in vitro test that requires a blood sample. The blood sample may be obtained by withdrawing blood by lancing a portion of his or her skin, using a lancing device, for example, to make blood available external to the skin, to obtain the necessary sample volume for in vitro testing. The fresh blood sample is then applied to an in vitro sensor, such as an analyte test strip, which is positioned in a meter or the like, whereupon suitable detection methods, such as calorimetric, electrochemical, or photometric detection methods, for example, may be used to determine the person's actual blood glucose level.

Available self-monitoring analyte systems generally include an analyte meter having a receptacle for receiving a cartridge containing a plurality of disposable analyte testing devices, e.g., test strips, which are individually and automatically dispensed on demand. An analyte test strip includes one or more chemical reagents designed to interact with a target analyte(s) in body fluid applied to it in such a way that an analyte meter connected to electrodes of the test strip can derive a value of the level of the target analyte contained in the body fluid. The meter may be an integrated device which provides a lancing function in addition to measuring the level of target analyte(s) in the body fluid being tested. Where the analyte test strips provide only a test component, the lancing is performed by a separate lancing mechanism housed within the meter. In other systems, the test strip may be integrated with a lancet into a single component, such as disclosed in U.S. patent application Ser. No. 12/488,181, herein incorporated by reference in its entirety. In either variation, the meter is configured to dispense the testing devices from the cartridge one at a time, as needed.

The test strip cartridge may include a biasing member at a loading end of the cartridge to bias the contained test strips towards the cartridge's strip-dispensing end. A seal is typically provided at the cartridge's strip-dispensing end for minimizing exposure of the test strips within the cartridge to ambient air. The seal is typically made of an elastomeric material configured to be released temporarily to permit loading of a test strip from the cartridge to within the meter for the lancing and testing processes. A desiccating material may be provided separately within the cartridge or integrated into the structural support of the cartridge to help maintain the analyte test devices substantially free of moisture. An advantage of an automatic test strip cartridge is that numerous analyte tests may be performed without having to manually load a new test strip for each test performed.

Examples of integrated lancing and testing systems are described in U.S. patent application Ser. Nos. 10/629,348, 10/701,993, 10/837,886, 10/899,773, 11/035,131, 11/146,897, 11/160,407, 11/160,427, 11/350,398, 11/535,985, 11/535,986, 11/830,760, 11/830,770, 11/830,779, 11/830,786, 11/831,649, 11/831,706, 11/868,762, 11/870,420 and 12/035,348, the disclosures of which are herein incorporated by reference.

Due to certain lot-to-lot inconsistencies in the test strip fabrication and manufacturing process, there may be variations in test strip sensitivity between lots which require some form of system calibration for each batch of strips. Currently, existing calibration mechanisms require the use of a calibration strip by the user, the inputting of a calibration code by the user, or the use of a machine readable mechanism on the strip or cartridge to modify the reaction interpretation of the meters for a particular lot of test strips.

Despite means for calibrating meters for given test strip lots, if a test strip is past its expiration date or its chemistry has otherwise degraded due to humidity and other constituents of the ambient atmosphere to which it has been exposed subsequent to fabrication and packaging and prior to actual use, i.e., during the test strip's shelf-life, unpredictable and unreliable analyte test results are likely. Moreover, during actual active use of a test strip cartridge, the cartridge is opened and closed by the meter each time a test strip is used, exposing the remaining test strips to an even higher level of ambient air, thereby contributing to degradation of the strips, even in the presence of a desiccating material within the cartridge.

SUMMARY OF THE INVENTION

The present invention includes analyte measurement systems, analyte measurement meters, analyte testing devices, cartridges thereof and integrated circuits for use therewith. The subject integrated circuits contain information and algorithms specific to the analyte testing devices contained within a cartridge. The meters are configured to communicate with the integrated circuit wherein such device-specific information and/or algorithms may be transferable between a meter and the integrated circuits. The present invention further includes methods related to the use of the integrated circuits and, in certain embodiments, to the counting or tracking of parameters related to the cartridges and analyte test devices.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 1 illustrates a distal perspective view of an exemplary meter of an analyte monitoring system of the present invention;

FIGS. 2A and 2B illustrate distal and proximal views, respectively, of a cartridge containing a plurality of analyte testing devices usable with the analyte meter of FIG. 1;

FIG. 5 provides an exemplary Calibration Log usable with the present invention.

DETAILED DESCRIPTION OF THE INVENTION

Figure 3:
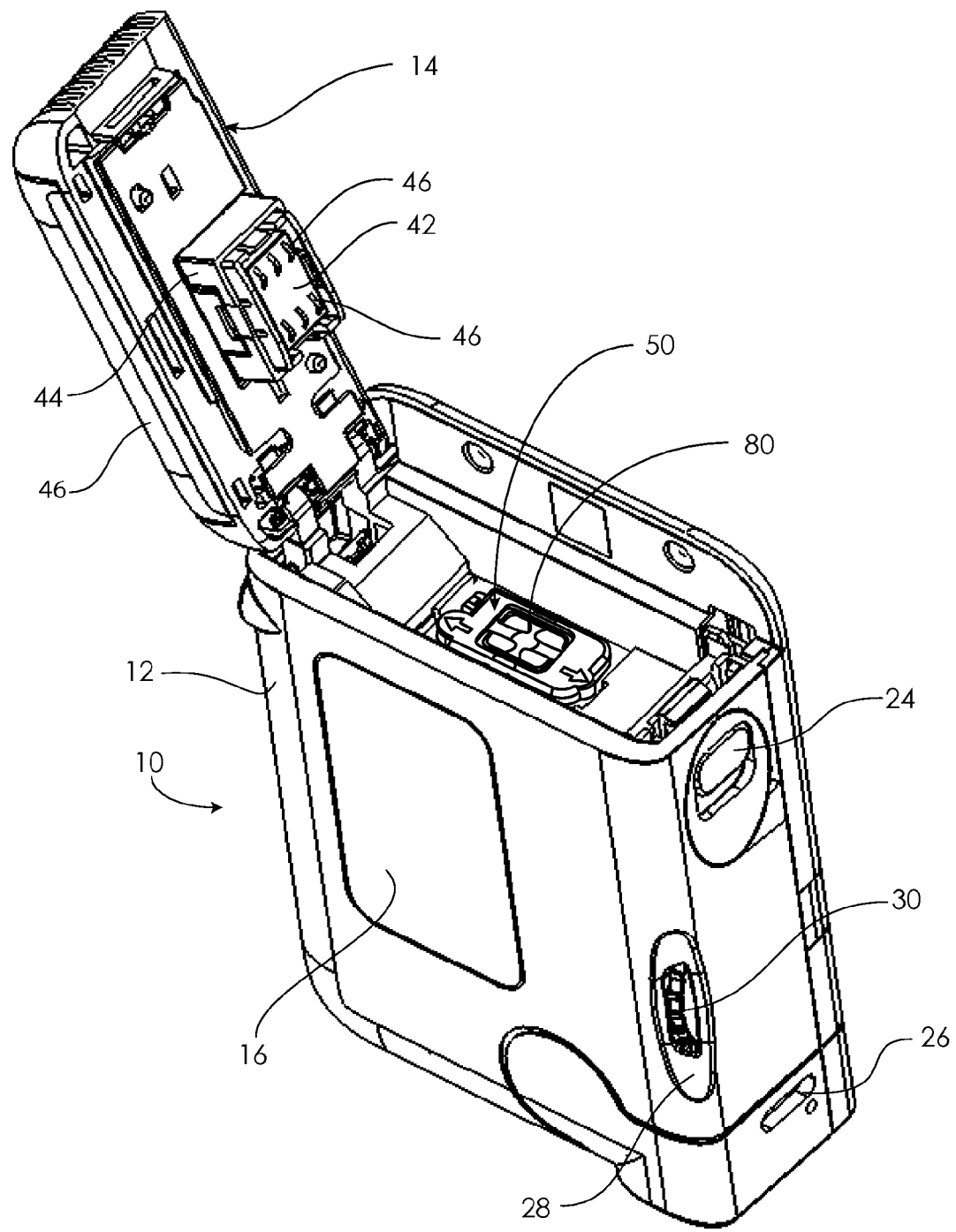
FIG. 3 illustrates an exemplary analyte measurement system of the present invention in which the cartridge of FIGS. 2A and 2B is operatively positioned within the meter of FIG. 1.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

As used herein and in the appended claims, the singular forms "a," "and," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The invention is now described in greater detail with respect to the system of FIGS. 1-4; however, such embodiment is merely exemplary as the features, advantages and objectives of the present invention apply to any type of analyte measurement system. The particular system embodiments described herein are particularly suitable for glucose measurement applications; however, the present invention may be used in any analyte measurement application.

Referring now to the figures, FIG. 1 provides a distal perspective view of a diagnostic device or meter 10 of the present invention. When referring to "distal" and "proximal" with respect to the components of the subject analyte systems and analyte testing devices, the term distal refers to the end which faces towards, contacts or is closest to the user's skin when in operative use and the term proximal refers to the end which faces away from or is furthest from the user's skin when in operative use. The exterior of meter 10 includes a housing 12 and a cartridge door 14 at a proximal end of the meter. Housed within door 14 under cover 46 are one or more batteries which provide power to the electronics and electronic motors which operate the device. Housing 12 contains various component assemblies of mechanical and electronic components, including but not limited to various components for directly interfacing with a cartridge 40, shown from distal and proximal perspective views in FIGS. 2A and 2B, respectively. Cartridge 40 contains a plurality of unused analyte testing devices, i.e., either test strips or strip-lancet combination devices (i.e., where the testing component and lancing component are at opposing ends of the "strip"). Reference to "strip" or "test strip" herein refers to either configuration.

The meter's mechanical components include various gears and motors for moving and orienting the analyte testing devices, to various operative positions relative to the housing. The electronic components include various printed circuit boards having circuitry for storing electronic data and running software programs for controlling and operating the device and measuring the target analyte in the extracted bodily fluid. On one side of meter 10, housing 12 frames a display 16, a navigation keypad 18 and a trigger button 20 which enable a user to interface with and operate the device. The various sidewalls of housing 12 frame various apertures including aperture 22 for receiving a cartridge door release latch 24, a test strip ejection slot 26, a recessed aperture 28 for receiving a thumb wheel 30 for adjusting the depth of a fluid expression cap or ring 32, and a switch 36 to disable or lock the meter against accidental button pushes when not in active use. Expression ring 32 is configured for engaging with a finger or other lancing site on the user's body to facilitate the expression of bodily fluid, e.g., blood, from the skin. A small test port 34 resides within expression ring 32 through which a lancet or lancet end of a strip (not shown) is advanced and retracted. The expression cap 32 resides within and is carried by a frame structure (not shown) which is mechanically coupled to a thumb wheel 46. Rotating thumb wheel 46 adjusts the vertical height of expression ring 32 relative to the lancet when in a lancing position. As the lancing stroke of the lancet is fixed, adjusting the relative height of the expression pad adjusts the location of the skin surface relative to the lance stroke allowing variable lancing depths to accommodate, for example, blood extraction at different sites on the body which may require varying lancing depths. An electronic communications port (not shown) may also provided by which an on-board microprocessor is accessed for programming, software download and off-board control.

Figure 4A:
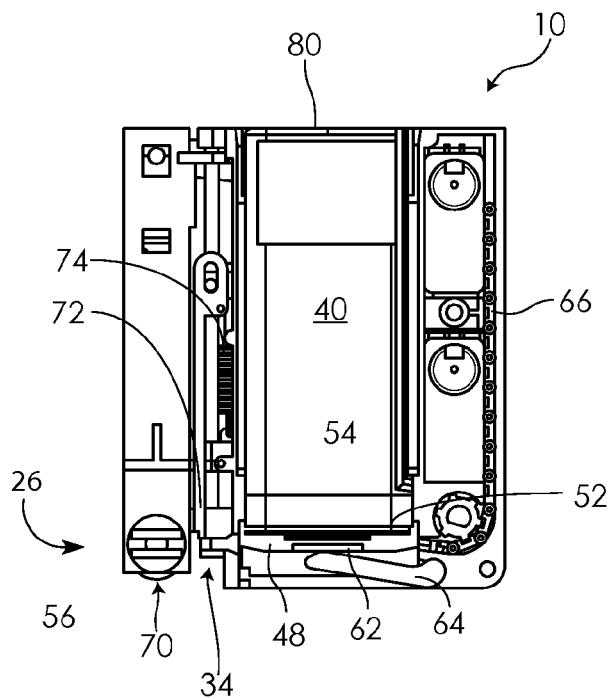
FIGS. 4A and 4B are side cross-sectional views of the analyte measurement system of FIG. 3 which illustrate an operational sequence of the system.
Figure 4B:
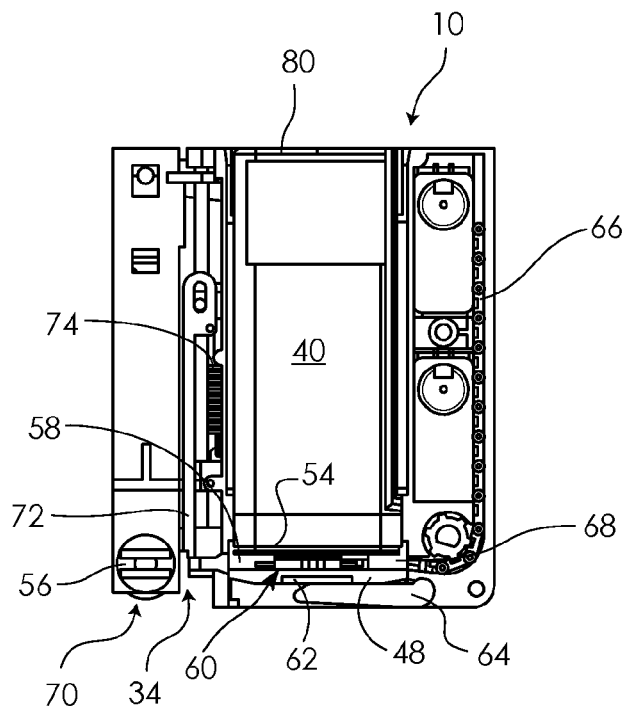

As shown in FIG. 3, the meter's cartridge door 14 opens to an interior compartment 38 in which the replaceable test strip cartridge 40 of FIGS. 2A and 2B is mechanically and electronically nested within meter 10. The cartridge door structure 14 contains a spring-loaded piston 42 which resides within the rectangular frame 44. A coil spring (not shown), for example, biases piston 42 which in turn, when door 14 is closed on the cartridge 40, biases the proximal end 50 of the cartridge downward against a tub 48, as shown in FIG. 4A, to create a hermetic seal at the cartridge's distal or strip-disposing end 52. An elastomeric seal 54, such as an O-ring type seal, may be provided around end 52 to further ensure the hermetic seal. When meter 10 is not in use or is in an inactive state, as shown in FIG. 4A, tub 48 is seated against elastomeric seal 54 by means of a lever 64, and the contained test strips are substantially protected against the ambient environment. When the meter 10 is activated to perform an analyte testing sequence, lever 64 briefly lowers tub 48, as shown in FIG. 4B, to allow for a single test strip or strip-lancet device 60 to exit the distal end 52 of cartridge 40 onto a positioning element 62, which centers the strip for precision loading onto a track 68, while the remaining unused test strips remain in the cartridge. For this brief amount of time, the cartridge is not sealed and the contained test strips are exposed to ambient air. A mechanism for sealing the cartridge upon removal from the meter may also be provided. In one embodiment, a spring-loaded latch may be provided with the cartridge. The latch may be mechanically opened when the cartridge is installed into the meter. The latch may spring shut sealing the cartridge when the cartridge is removed from the meter. Alternatively, the latch may be manually closed with or without the assistance of a spring. In another embodiment, a separate sealing attachment may be provided to a user who may install the attachment to seal the cartridge upon removal from the meter. In any of these ways, effects of exposure to ambient air may be mitigated during the time that the cartridge is removed from the meter.

Upon the release of an unused test strip 60 from cartridge 40, a pusher mechanism 66 residing within track 68 engages the test strip and advances it into a slot within rotatable turret 56 which, as shown in FIG. 4B, is aligned horizontally for receiving a test strip from the distal end 52 of cartridge 40, which horizontal position also aligns the slot with strip ejection port 26 for ejection after the analyte analysis has been completed. Once within slot 56, strip 60 is in electrical contact with the meter's electronics. Turret 56 is then rotated 90° or to the extent necessary for axial alignment with the lancet driving mechanism 74. In embodiments where the testing component and lancet are integrated within a single strip, a blade or lever 72 is then driven downward for uncapping a lancet. The lancet or lancet end of the strip is advanced through test port 34 for lancing the skin. The strip is then retreated and is rotated or flipped by 180° (or as necessary) as it remains within the turret slot 56. The test strip or the testing end of the strip is then advanced again through the port 34 again and is made to contact the expressed bodily fluid, e.g., blood. The signal generated by the electrochemical interaction between the strip's sensing chemistry and the target analyte, e.g., glucose, is received by the meter electronics and the evaluated to provide the level of analyte in the fluid sample. The lancet cap may then be recapped over the lancet, if applicable. After testing, the strip is rotated 90° (or as necessary) to align with and be ejected through ejection port 26. Pusher 66 may be used a second time for assisting in the ejection of the used and recapped strip Referring back to FIG. 3, in addition to applying a bias to cartridge 40, the spring loaded piston 42 within cartridge door 14 simultaneously serves as the electrical interface between meter 10 and cartridge 40 by way of a plurality of electrical contacts 46 which electrically couple the meter electronics with an integrated circuit (IC) 80, e.g., EEPROM or the like, which is sometimes referred to as a "smart chip." Chip 80 is mounted to the external proximal end 50 of cartridge 40; however, it may be mounted at any suitable location on cartridge 40. In other embodiments, chip 80 may be located internally to the cartridge or on a test strip contained therein, and may interface with meter 10 via RF or other wireless or optical communication means.

The smart chip 80 includes non-volatile memory storage for storing and communicating information and data about the test strips and/or cartridge 40 to the meter 10, including but not limited to test strip serial and batch numbers, date and time of manufacture, expiration date, etc. Also stored on chip 80 are one or more algorithms for calibrating meter 10 to properly analyze fluid samples applied to the enclosed batch of test strips. The system is further programmed to separately track information for different strips or groups of strips, such as may be contained in cartridges, vials or other types of containers of analyte test devices. As an associated chip distinguishes each cartridge container of strips, a meter may discriminate between different groups or containers of strips by reading the chip each time the meter is powered-up to perform a glucose test using a strip from a certain container or cartridge of strips.

Strips are manufactured in lots within which the strips have the same or substantially similar chemistry. Strips of different lots, however, may differ significantly which is why the lot information may be provided for each cartridge of strips. As lots of strips are produced, the smart chip information may be customized accordingly. This provides the flexibility to support on-going changes in strip design. For example, if an advantageous mediator for the strips is discovered, changes to the algorithm that supports the new mediator can be made through changing the parameters in the chip alone without having to modify the meter. The processor chip may also be programmed to receive information from the meter about the meter itself, including, for example, the meter serial number, etc. The chip also includes processing components, such as clocks or counters, for example, for tracking the number of unused strips remaining in the cartridge and for timing various events, such as the duration of time the cartridge is operatively positioned in the meter, tub open time, etc., many of which are described in greater detail below.

Given the importance of reliable glucose test results in a self-care regimen, the cartridges and/or meters may have one or more desiccating components to inhibit degradation of the test strips by moisture they may be exposed to. As mentioned previously, when the cartridge is unsealed to remove a strip for testing, however, the strips remaining in the cartridge are exposed to the ambient air. When the cartridge is again sealed after removal of the strip for testing, the desiccating components dry out the inner cartridge to a state that continues until the cartridge is unsealed for another test.

The cartridge-specific processor chips of the present invention are configured to precisely track or count certain parameters which may vary over time and to track or clock time passage of certain conditions of exposure to ambient air. The various counted/timed parameters may have an integer value, e.g., a number of strips, hours, days, etc. which is either increased or decreased by 1 (or another integer as otherwise programmed) upon the occurrence of a certain event, e.g., the performance of an analyte test, or may be an accumulation of time, e.g., in days, hours and/or seconds.

Various counted/timed parameters which may be provided by the subject cartridge chips are now described in greater detail, many of which are provided for the purpose of preventing the use of test strips which have expired due to the passage of time and/or due to the overexposure to ambient air. The system/chip may be configured such that the meter and/or cartridge becomes inoperable when one or more of these counted/time parameters reach a maximum value. In other words, inoperability may be achieved by any one of the parameters reaching its respective maximum value or based on a summation of two or more parameters at any given time. Alternatively, the meter and cartridge may continue to function upon a determination that the contained test strips have expired, but the data obtained from analyte tests with these expired strips will be flagged by the system accordingly.

(1) Time Zero ($T_0$) is the designated baseline time programmed into the chip which may be the date/time of manufacture of the test strip lot, the date/time at which the cartridge is packaged, or the date/time the cartridge is first installed into a meter, or various starting times may be employed depending on the counting/timing function employed. Many of the system's counting and timing algorithms are initiated at $T_0$.

(2) Expiration Time/Date counts or tracks the number of days (either as an integer or in days/hours/seconds) continuously from $T_0$ at which point the cartridge would become inoperable, or the meter would not be able to perform a test with any of the strips remaining in the cartridge. Alternatively, when the Expiration Time/Date is reached, the system provides an audio or visual warning to the user that indicates that any further tests made with the remaining test strips may not be reliable, or would not incorporate such test results therefrom among those compiled for purposes of analytical reporting. In certain embodiments, there may be multiple expiration dates/times, e.g., a first time where a warning is provided that the test may be unreliable, a second time later than the first time where a test can be performed but with a warning and where the results are not kept for analytical graphs and/or logging, and a third time later than each of the first and second times where a test simply cannot be performed with a strip from the expired cartridge. One or more additional expiration dates/times can be set that are sum periods of heavy ambient exposure, i.e., having faster rates of degradation, as will be further described below. The system may be programmed to allow testing with expired strips, but preferably with user confirmation of such.

(3) Tub Open Time counts, after insertion of the cartridge into the meter, the number of times the meter's tub is lowered or opened from the cartridge to load an analyte testing device (as in shown in FIG. 4B) and/or the accumulated time in which the tub is in the lowered or opened position, i.e., the accumulated time which the contained test strips are exposed to ambient air. In certain embodiments, the systems are programmed to discriminate and separately track between periods of varying degradation rates. When test strips are directly exposed to ambient air, i.e., when the tub is in the lowered or open position, the test strips experience relatively faster rate of degradation as compared to when test strips are sealed within a desiccated environment, i.e., after a cartridge is removed from its packaging and placed within a meter, but with the tub in the up or closed position. Thus, the periods of time during which the cartridge is unsealed are periods of strong/faster degradation, while the periods of time during which the cartridge is sealed and desiccated are periods of somewhat weaker/slower degradation.

(4) Usage Days counts the number of days a cartridge is used and may be measured continuously from either removal of the cartridge from its original packaging or upon insertion of the cartridge into a meter, whether or not the cartridge is removed (with one or more strips remaining) and replaced into the same meter any number of times. The system may be configured to presume that a cartridge is sealed during the entire time from manufacture to insertion into the meter. That is, the time from unsealing of a fresh cartridge until insertion and sealing within the meter may be neglected. Alternatively, the system may track this interim unsealed time for purposes of determining expiration the contained test strips (see Cartridge Removed Time below). For example, an electrical connection may be broken when the cartridge is unsealed which initiates a counter or clock that is stopped when the cartridge is sealed into the meter, or the time may be estimated by a user and manually entered, or a timer may be started on the meter by the user when the fresh cartridge is about to be unsealed which is then stopped like a stopwatch when the cartridge is sealed within the meter. This interim time may also be added to Tub Open Time or accounted for separately as a period of strong degradation.

(5) Cartridge Removed Time may track any time between removal of the cartridge from the meter and its replacement back into the meter. This may be particularly relevant in embodiments where the cartridge does not have a self-sealing mechanism, such as a latch or the like, that allows it to be hermetically sealed (after removal from its hermetically sealed packaging). An algorithm may be employed which adds the Cartridge Removed Time to Tub Open Time for purposes of determining whether a maximum exposure threshold time has been reached. That is, the effect of exposure of the analyte testing devices in the cartridge may be counted the same whether the tub is open for an installed cartridge or the cartridge is removed from the meter. This time may also be added to Tub Open Time or accounted for separately as a period of strong degradation. As such multiple expiration clocks may be kept, wherein the cartridge is deemed expired when the first of these runs out, or a combination may be used such as counting the periods of stronger degradation as having a weighted value, e.g., twice or three times the degradation effect as compared to periods of weaker degradation. Alternatively, one or more of the counters/timers may be summed together or otherwise counting down to expiration.

(6) Remaining Tub Open Time represents the total amount of time the strips are still allowed to be unsealed while in the meter where a certain amount of Tub Open Time is counted down to expiration independently of any other expiration tracking. This parameter may be an integer in minutes and/or seconds which is decremented as the Tub Open Time is incremented. When the Remaining Tub Open Time reaches zero, the cartridge will be expired (if it hasn't already expired due to expiration based on total time from manufacture and/or total time since installation of the cartridge into the meter). A Current Tub Open Time may also (or alternatively) be tracked representing the total amount of time the strips have been unsealed while in the meter (and perhaps otherwise, see above).

(7) Analyte Testing Devices Remaining indicates the number of unused devices, e.g., test strips, which remain in the cartridge. The initial total number of device may be recorded onto the chip which number is decremented each time a test strip is advanced out of the cartridge or each time the tub is opened. Although the meter may not be able to perform a test when the cartridge is empty, the meter may still power-on to perform analyses and reporting functions, e.g., the user may review results such as graphs and log entries. Examples of such are disclosed in U.S. patent application Ser. No. 12/233, 584, which is incorporated by reference in its entirety.

(8) Allowable Days for Cartridge in Device represents the amount of time the cartridge can be stored within the meter before the strips may be deemed to provide unreliable or inaccurate results. This parameter may be an integer of days. The cartridge may be deemed to expire when either the Remaining Tub Open Time or the Allowable Days For Cartridge in Device has expired, whichever is earlier, or some combination of the two, or including a time from manufacture of the cartridge as a third expiration period that is kept separately or in combination with the others.

(9) Error Detection/Correction/Data Integrity. An error detection and/or error correction and/or data integrity protocol(s) may be employed. For example, a Cyclic redundancy check (CRC), or the like, may be performed periodically or on-demand by the user to ensure the integrity of the data stored on the chip or the chip's reader.

(10) Cartridge/Meter Unique Identifier. When a new cartridge is installed into a meter, a unique identifier of the meter, e.g., a serial number or the like, is transferred and recorded on the cartridge chip. This feature mitigates incorrect counting and tracking of parameters by previously or partially used cartridges. For example, when a partially used cartridge is installed in a meter, the meter identifier previously stored on the cartridge chip is compared to the current meter's identifier. If they are the same, then the cartridge is the last one installed and the various counted/time parameters can be updated accordingly. If they are not the same, then the cartridge is not the last one installed on that particular meter and a new Cartridge Log (described in greater detail below) may be created and stored. The systems may also be configured such that the subject meters record and store a unique identifier from each new cartridge installed into it and creating a Cartridge Log for each unique cartridge identifier. The system may also be configured to maintain a count of new cartridges installed in the meter over its lifetime or for a designated period of time, referred to as New Cartridge Count.

(11) Control Solution Range Delta provides the meter with the information necessary to determine the correct range for control solution test values for a particular lot of test strips. Any number of these range values, depending on the type of different control solutions that may be used to check the integrity of the test strips. For example, there may be three values, one for each of three possible control solutions. The meter will read the delta value for the control solution test selected and use it to adjust the expected range to determine if the measured value falls within.

(12) Cartridge Log. In addition to reading and modifying the cartridge's processor chip, as described above, there may be a Cartridge Log created in the meter's non-volatile memory for each cartridge installed in order to optimize system performance. Additionally, certain of the cumulative cartridge data may be used to analyze user compliance history, trends, etc. FIG. 5 illustrates an embodiment of a Cartridge Log usable with the present invention where data (e.g., counts, clocked time, identifiers, and any of the parameters discussed herein) in the Log are assigned a byte number and recorded in bit format. Other information not listed in the Log of FIG. 5 may also be stored in the log. A Cartridge Log may be updated periodically, e.g., daily or with each analyte test performed by the meter. If an installed cartridge is removed and then reinstalled at a later time, its original Cartridge Log data is updated or a new Cartridge Log may be created with its status set to Used. Additionally, a partially used cartridge installed from another meter will generated a new Cartridge Log for that cartridge with a status identifier of Used and Expired. When the meter's memory capacity designated for storing Cartridge Logs becomes full, the oldest Cartridge Log may be overwritten. Empty cartridges or cartridges with chips that cannot be read may not alter the Cartridge Log or the New Cartridge Count. Test results obtained from tests conducted with expired strips may be recorded in the Cartridge Log, but are identified as coming from expired strips. The Cartridge Log may also be updated to include the date and time the cartridge is removed.

(13) Calibration Algorithm/Code. The cartridge chip may further provide a Calibration Algorithm which includes a calibration code and other data for calibrating the meter to optimally perform for the particular lot of analyte testing devices contained within the cartridge. Alternatively, the Calibration Algorithm or Code may be separately provided on a bar code, a RFID tag, a label, or otherwise may be located on individual strips contained in the cartridge or vial. U.S. patent application Ser. No. 11/350,398, incorporated by reference in its entirety, provides further examples of alternative embodiments for purposes of calibration. For example, there may be contact pads that may be shorted together or kept apart during a test strip manufacturing process in order to communicate a calibration code to the meter. Alternatively, there may be a set of contact pads and a varying resistance between the two pads where the resistance is changed during the manufacturing process of the test strips to communicate a calibration code to the meter. These alternatives may be provided along with an electrical memory that is readable and writable by the meter, which communicates a calibration code to the meter, and can carry other information such as strip expiration and/or a strip number count down and/or other features described with regard to the smart chips of the present invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An analyte measurement system comprising:
   a meter; and
   one or more cartridges of analyte testing devices, each cartridge comprising an integrated circuit coupled thereto and having stored thereon information specific to the analyte testing devices within the cartridge, and wherein the meter is configured to communicate with the integrated circuit to access the information stored therein, and wherein the system is configured to track at least one analyte testing device degradation parameter;
   wherein the meter comprises a compartment therein for operatively receiving a cartridge therein and a mechanism for selectively maintaining a hermetic seal on the cartridge, wherein a degradation parameter comprises the cumulative time the cartridge is unsealed.

2. The analyte measurement system of claim 1, wherein a degradation parameter comprises the cumulative time an interior of the cartridge is exposed to ambient air.

3. The analyte measurement system of claim 1, wherein the system is configured to track a plurality of degradation parameters having varying degradation rates.

4. The analyte measurement system of claim 1, wherein a second degradation parameter comprises the cumulative time a cartridge is received within the meter compartment.

5. The analyte measurement system of claim 1, wherein a second degradation parameter comprises the cumulative time a cartridge is removed from the meter compartment subsequent to an initial installation therein.

6. The analyte measurement system of claim 1, wherein a second degradation parameter comprises the cumulative time between packaging of a cartridge and installation into the meter.

7. The analyte measurement system of claim 1, wherein the information further comprises the number of analyte testing devices contained within a cartridge upon installation into a meter.

8. The analyte measurement system of claim 7, wherein the system is further configured to decrement the number of analyte testing devices upon use of an analyte testing device.

9. The analyte measurement system of claim 1, wherein the meter is configured to separately track information relating to multiple cartridges.

10. The analyte measurement system of claim 9, wherein the meter is configured to update information relating to a cartridge that has been installed, removed and reinstalled in the meter, whether or not a second cartridge is installed and removed from the meter in the interim.

11. The analyte measurement system of claim 1, wherein a unique meter identifier is stored on the integrated circuit upon installation of a cartridge into the meter.

12. The analyte measurement system of claim 1, wherein the system is configured to track the expiration of the analyte testing devices from a fixed date.

13. The analyte measurement system of claim 1, wherein the meter is configured to electrically contact the integrated circuit.

14. The analyte measurement system of claim 1, wherein the meter comprises an RF transmitter/receiver for communicating with the integrated circuit.

15. The analyte measurement system of claim 1, wherein the information further comprises a calibration algorithm for calibrating the meter for proper use of the analyte testing devices.

16. The analyte measurement system of claim 1, wherein the information further comprises parameters relating to chemistry provided on the analyte testing devices, wherein the parameters are modifiable.

17. The analyte measurement system of claim 1, wherein the analyte testing devices comprise only an analyte testing component.

18. The analyte measurement system of claim 1, wherein the analyte testing devices comprise a lancet integrated with an analyte testing component.

19. The analyte measurement system of claim 1, wherein the system is configured to measure blood glucose.

20. A cartridge for containing a plurality of analyte testing devices and for operably coupling to an analyte meter, the cartridge comprising:
   an integrated circuit coupled to the cartridge, the integrated circuit comprising at least one algorithm for tracking at least one analyte testing device degradation parameter;
   wherein the integrated circuit is configured to communicate with an analyte measurement meter that operatively receives the cartridge therein and that includes a mechanism for selectively maintaining a hermetic seal on the cartridge;
   wherein the cartridge is hermetically resealable, and wherein the at least one analyte testing device degradation parameter comprises the cumulative time the cartridge is unsealed between resealings.

21. The cartridge of claim 20, wherein the at least one algorithm is dependent upon the occurrence of at least one type of action performed by the meter.

22. The cartridge of claim 21, wherein the type of action comprises unsealing of the cartridge.

23. The cartridge of claim 20, wherein the at least one analyte testing device degradation parameter comprises cumulative time of exposure to ambient air.

24. The cartridge of claim 20, wherein the at least one analyte testing device degradation parameter comprises cumulative time subsequent to unpackaging of the cartridge.

25. The cartridge of claim 20, wherein the at least one analyte testing device degradation parameter comprises cumulative time subsequent to installation of the cartridge into a meter.

26. The cartridge of claim 20, wherein the algorithm subtracts cumulative time of exposure to ambient air from cumulative time subsequent to installation of the cartridge.

27. The cartridge of claim 20, wherein the at least one analyte testing device degradation parameter comprises time subsequent to installation of the cartridge into a meter.

28. The cartridge of claim 20, wherein the at least one analyte testing device degradation parameter comprises time subsequent to manufacture of the analyte testing devices.

29. The cartridge of claim 20, wherein the integrated circuit comprises an algorithm for separately tracking at least two analyte testing device degradation parameters.

30. The cartridge of claim 29, wherein the at least two degradation parameters have varying rates of degradation.

31. The cartridge of claim 20, wherein the integrated circuit comprises a unique identifier such that the integrated circuit is uniquely identifiable by a meter from integrated circuits of amongst a plurality of cartridges, wherein the meters are configured to separately track information relating to a plurality of cartridges.

32. The cartridge of claim 20, wherein the integrated circuit is writeable to record a unique identifier for each meter into which the cartridge is installed.

33. The cartridge of claim 20, wherein the integrated circuit further comprises conducting contacts to couple directly with electrodes of an analyte measurement meter to communicate with the meter when the cartridge is installed in the meter.

34. The cartridge of claim 20, wherein the integrated circuit further comprises an RF transmitter/receiver for communicating with an analyte measurement meter.

35. The cartridge of claim 20, wherein the integrated circuit further comprises calibration information about the analyte testing devices.

36. The cartridge of claim 20, wherein the integrated circuit further comprises expiry information about the analyte testing devices.

37. The cartridge of claim 20, wherein the integrated circuit further comprises a value for an initial number of analyte testing devices and an algorithm for decrementing that value upon use of an analyte testing device.

38. The cartridge of claim 20, wherein the integrated circuit further comprises parameters relating to chemistry provided on the analyte testing devices, wherein the parameters are modifiable.

39. The cartridge of claim 20, wherein the integrated circuit further comprises at least one algorithm for calibrating a meter for proper use with the plurality of analyte testing devices contained in the cartridge.

40. A method of tracking at least one degradation parameter for analyte testing devices dispensable from within a sealed cartridge having an integrated circuit coupled thereto and installable within an analyte measurement meter communicable therewith, the method, upon installation of the cartridge within the meter, comprising:
communicating with the integrated circuit and accessing the at least one degradation parameter; and
updating the at least one degradation parameter based on at least one type of action performed by the meter;
wherein the updating comprises summing at least two degradation parameters.

41. The method of 40, wherein:
a first degradation parameter comprises cumulative time the analyte testing devices are exposed to ambient air; and
a first type of action comprises temporarily unsealing the cartridge.

42. The method of 41, wherein:
a second degradation parameter comprises cumulative time the analyte testing devices are exposed to desiccated conditions, wherein the cartridge comprises a desiccating material; and
a second type of action comprises receiving the cartridge in the meter.

43. The method of claim 40, further comprising decrementing a parameter stored on the integrated circuit representing the number of analyte testing devices contained in the cartridge.

44. The method of claim 40, further comprising calibrating the meter according to calibration parameters stored on the integrated circuit.

45. The method of claim 40, further comprising creating a modifiable log of information about the cartridge and the analyte testing devices contained therein.

46. The method of claim 40, further comprising commencing the timing of expiry of the analyte testing devices.

47. The method of claim 40, further comprising storing a unique meter identifier onto the integrated circuit.

48. The method of claim 40, further comprising storing a unique cartridge identifier onto the meter.

49. A method of analyte testing calibration for a lot of analyte testing devices contained within a cartridge configured for installation into an analyte testing meter, the method comprising:
storing information specific to the lot of analyte testing devices onto an integrated circuit associated with the cartridge, the information including a cartridge identifier;
installing the cartridge into the meter, wherein the meter is in communication with the integrated circuit;
storing the cartridge identifier onto the meter from the integrated circuit;
calibrating the meter for using the analyte testing devices associated with the cartridge identifier; and
tracking at least one analyte testing device degradation parameter, wherein the meter comprises a compartment therein for operatively receiving the cartridge therein and a mechanism for selectively maintaining a hermetic seal on the cartridge, and wherein the degradation parameter comprises the cumulative time the cartridge is unsealed.

50. The method of claim 49, further comprising creating on the meter a log of information specific to the cartridge.

51. The method of claim 50, further comprising updating the log of information upon using an analyte testing device.

52. The method of claim 51, further comprising removing the cartridge from the meter and updating the log of information upon subsequent reinstallation of the cartridge into the meter.

* * * * *